(12) United States Patent
Zhou et al.

(10) Patent No.: US 9,777,073 B2
(45) Date of Patent: *Oct. 3, 2017

(54) CONSTRUCTION AND APPLICATION OF BISPECIFIC ANTIBODY EPCAM×CD3

(71) Applicant: Wuhan YZY Biopharma Co., Ltd., Hubei (CN)

(72) Inventors: Pengfei Zhou, Hubei (CN); Tao Wang, Hubei (CN); Lijuan Fang, Hubei (CN); Liu Hu, Hubei (CN); Yang Liu, Hubei (CN); Yu Zhang, Hubei (CN); Kesuo Fan, Hubei (CN)

(73) Assignee: Wuhan YZY Biopharma Co., Ltd., Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/803,298

(22) Filed: Jul. 20, 2015

(65) Prior Publication Data

US 2016/0090426 A1 Mar. 31, 2016

(30) Foreign Application Priority Data

Jul. 21, 2014 (WO) ................ PCT/CN2014/082590
Jan. 21, 2015 (CN) .......................... 2015 1 0031516

(51) Int. Cl.
*C07K 16/30* (2006.01)
*C07K 16/46* (2006.01)
*C07K 16/28* (2006.01)

(52) U.S. Cl.
CPC ........ *C07K 16/468* (2013.01); *C07K 16/2809* (2013.01); *C07K 16/2878* (2013.01); *C07K 16/2887* (2013.01); *C07K 16/30* (2013.01); *C07K 2317/526* (2013.01); *C07K 2317/60* (2013.01); *C07K 2317/622* (2013.01); *C07K 2317/73* (2013.01); *C07K 2317/92* (2013.01); *C07K 2317/94* (2013.01)

(58) Field of Classification Search
CPC .. C07K 16/468; C07K 16/32; C07K 16/2809; C07K 2317/31; C07K 2317/622; C12N 15/79–15/85

See application file for complete search history.

(56) References Cited

U.S. PATENT DOCUMENTS

| | | | | |
|---|---|---|---|---|
| 9,079,965 B2 * | 7/2015 | Zhou | ...................... | C07K 16/32 |
| 9,562,110 B2 * | 2/2017 | Zhou | ...................... | C07K 16/32 |
| 2010/0286374 A1 * | 11/2010 | Kannan | ................ | C07K 16/468 |
| | | | | 530/387.3 |
| 2014/0112914 A1 * | 4/2014 | Nezu | ...................... | C07K 16/30 |
| | | | | 424/133.1 |
| 2015/0284475 A1 * | 10/2015 | Zhou | ...................... | C07K 16/32 |
| | | | | 424/135.1 |
| 2016/0145339 A1 * | 5/2016 | Zhou | .................. | C07K 16/2809 |
| | | | | 530/387.3 |

FOREIGN PATENT DOCUMENTS

JP 3587881 11/2004
WO WO2014079000 5/2014

OTHER PUBLICATIONS

He Freedom(TM) CHO-S(TM) Kit User Guide, Thermo Fisher Scientific, Publication No. MAN0003505, 2015.*
Muda et al., Protein Eng. Design Selection, May 2011; 24(5):447-54.*
Ahmad, Z. et al, "ScFv antibody: Principles and clinical application", Clinical and Developmental Immunology, vol. 2012, pp. 1-15, Article No. 980250, DOI:10.1155/2012/980250, (2012).
Michaelson, J. et al, "Anti-tumor activity of stability-engineered IgG-like bispecific antibodies targeting TRAIL-R2 and LTbetaR", mAbs, vol. 1:2::128-141, (Mar.-Apr. 2009).
Kranz, D. et al, "Partial elucidation of an anti-hapten repertoire in BALB/c mice: comparative characterization of several monoclonal antifluorescyl antibodies", Mol Immunol. 18:10:889-898, (1981).

* cited by examiner

*Primary Examiner* — Jessica H Roark
(74) *Attorney, Agent, or Firm* — Sheppard Mullin RIchter & Hampton LLP

(57) ABSTRACT

The present invention provides a bispecific antibody. The bispecific antibody provided by the present invention comprises a single-chain unit and a monovalent unit, wherein the single-chain unit has a specific binding capability against surface antigen CD3 of an immune cell; the monovalent unit has a specific binding capability against the surface antigen EpCAM of a tumor cell; the single-chain unit comprises a single-chain variable fragment ScFv fused with an Fc fragment; and the monovalent unit comprises a light chain and heavy chain pair. The present invention also provides a preparation method of the bispecific antibody and pharmaceutical use of these antibodies.

2 Claims, 8 Drawing Sheets

SEQUENCE LISTING

<160> NUMBER OF SEQ ID NOS: 20

<210> SEQ ID NO 1
<211> LENGTH: 450
<212> TYPE: PRT
<213> ORGANISM: Homo sapiens

<400> SEQUENCE: 1

```
Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Asp Thr Thr Pro Pro Val
385                 390                 395                 400

Leu Asp Ser Asp Gly Ser Phe Phe Leu Tyr Ser Asp Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 1353
<212> TYPE: DNA
<213> ORGANISM: Homo sapiens

<400> SEQUENCE: 2
gaggtgcagc tgctcgagca gtctggagct gagctggtaa ggcctgggac ttcagtgaag      60
atatcctgca aggcttctgg atacgccttc actaactact ggctaggttg ggtaaagcag     120
aggcctggac atggacttga gtggattgga gatattttcc ctggaagtgg taatatccac     180
tacaatgaga agttcaaggg caaagccaca ctgactgcag acaaatcttc gagcacagcc     240
tatatgcagc tcagtagcct gacatttgag gactctgctg tctatttctg tgcaagactg     300
aggaactggg acgagcctat ggactactgg ggccaaggga ccacggtcac cgtctcctcc     360
gcgtcgacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
```

```
gagtacaagt gcaaggtctc aacaaagcc ctcccagccc ccatcgagaa aaccatctcc    1020
aaagccaaag gcagcccccg agaaccacag gtctacaccc tgcccccatc ccgggatgag    1080
ctgaccaaga accaggtcag cctgtggtgc ctggtcaaag gcttctatcc cagcgacatc    1140
gccgtggagt gggagagcaa tgggcagccg gagaacaact acgataccac gcctcccgtg    1200
ctggactccg acggctcctt cttcctctac agcgatctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                1353
```

```
<210> SEQ ID NO 3
<211> LENGTH: 220
<212> TYPE: PRT
<213> ORGANISM: Homo sapiens

<400> SEQUENCE: 3

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 4
<211> LENGTH: 663
<212> TYPE: DNA
<213> ORGANISM: Homo sapiens

<400> SEQUENCE: 4
gagctcgtga tgacacagtc tccatcctcc ctgactgtga cagcaggaga gaaggtcact    60
atgagctgca gtccagtca gagtctgtta aacagtggaa atcaaaagaa ctacttgacc    120
tggtaccagc agaaaccagg gcagcctcct aaactgttga tctactgggc atccactagg    180
gaatctgggg tccctgatcg cttcacaggc agtggatctg gaacagattt cactctcacc    240
```

-continued

```
atcagcagtg tgcaggctga agacctggca gtttattact gtcagaatga ttatagttat    300
ccgctcacgt tcggtgctgg gaccaagctt gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
tag                                                                  663
```

<210> SEQ ID NO 5
<211> LENGTH: 477
<212> TYPE: PRT
<213> ORGANISM: Homo sapiens
<400> SEQUENCE: 5

```
Gln Val Gln Leu Gln Gln Ser Gly Ala Glu Leu Ala Arg Pro Gly Ala
  1               5                  10                  15

Ser Val Lys Met Ser Cys Lys Ala Ser Gly Tyr Thr Phe Thr Arg Tyr
                 20                  25                  30

Thr Met His Trp Val Lys Gln Arg Pro Gly Gln Gly Leu Glu Trp Ile
             35                  40                  45

Gly Tyr Ile Asn Pro Ser Arg Gly Tyr Thr Asn Tyr Asn Gln Lys Phe
         50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser Gly Gly Gly Ser Gly Gly Gly Gly
            115                 120                 125

Ser Gly Gly Gly Gly Ser Gln Ile Val Leu Thr Gln Ser Pro Ala Ile
        130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240

Arg Gly Ala Ala Ala Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285
```

```
Val Thr Cys Val Val Val Asp Val Ser His Glu Asp Pro Glu Val Lys
    290                 295                 300
Phe Asn Trp Tyr Val Asp Gly Val Glu Val His Asn Ala Lys Thr Lys
305                 310                 315                 320
Pro Arg Glu Glu Gln Tyr Asn Ser Thr Tyr Arg Val Val Ser Val Leu
                325                 330                 335
Thr Val Leu His Gln Asp Trp Leu Asn Gly Lys Glu Tyr Lys Cys Lys
            340                 345                 350
Val Ser Asn Lys Ala Leu Pro Ala Pro Ile Glu Lys Thr Ile Ser Lys
        355                 360                 365
Ala Lys Gly Gln Pro Arg Glu Pro Gln Val Tyr Thr Leu Pro Pro Ser
370                 375                 380
Arg Asp Glu Leu Thr Lys Asn Gln Val Ser Leu Thr Cys Leu Val Lys
385                 390                 395                 400
Gly Phe Tyr Pro Ser Asp Ile Ala Val Glu Trp Glu Ser Asn Gly Gln
                405                 410                 415
Pro Glu Asn Asn Tyr Lys Thr Thr Pro Pro Val Leu Asp Ser Asp Gly
            420                 425                 430
Ser Phe Phe Leu Tyr Ser Lys Leu Thr Val Asp Lys Ser Arg Trp Gln
        435                 440                 445
Gln Gly Asn Val Phe Ser Cys Ser Val Met His Glu Ala Leu His Asn
450                 455                 460
His Tyr Thr Gln Lys Ser Leu Ser Leu Ser Pro Gly Lys
465                 470                 475

<210> SEQ ID NO 6
<211> LENGTH: 1434
<212> TYPE: DNA
<213> ORGANISM: Homo sapiens

<400> SEQUENCE: 6
caggtgcagc tggtgcagag cggcggcggc gtcgtgcagc cgggcaggtc cctgagactg      60
tcttgtaagg cttctggata caccttcact agatacacaa tgcactgggt cagacaggct    120
cctggaaagg gactcgagtg gattggatac attaatccta gcagaggtta tactaactac    180
aatcagaagt ttaaggacag attcacaatt tctactgaca atctaagag tacagccttc     240 ctgcagatgg actcactcag acctgaggat accggagtct attttgtgc tagatattac     300 gatgaccact actgtctgga ctactggggc caaggtaccc cggtcaccgt gagctcagga    360
ggcggcggtt caggcggagg tggaagtggt ggaggaggtt ctgatattca gatgacccag    420
agcccgtcaa gcttatctgc ttctgtcgga cagagtca caatcacatg ttctgcttct      480
agctctgtct cttacatgaa ctggtatcag cagacacctg gaaaggctcc taagcggtgg    540
atctacgaca catctaagct cgcttctgga gtcccttcta gattctctgg ttctggctct    600
ggaacagact acacattcac aatctcttct ctccaacctg aggacatcgc tacatactac    660
tgccaacagt ggtctagcaa tccttttcaca ttcggacagg gtaccaaact gcagatcaca    720
agaggtgcgg ccgcagagcc caaatcttgt gacaaaactc acacatgccc accgtgccca    780
gcacctgaac tcctgggggg accgtcagtc ttcctcttcc ccccaaaacc caaggacacc    840
ctcatgatct cccggacccc tgaggtcaca tgcgtggtgg tggacgtgag ccacgaagac    900
cctgaggtca agttcaactg gtacgtggac ggcgtggagg tgcataatgc caagacaaag    960
ccgcgggagg agcagtacaa cagcacgtac cgtgtggtca gcgtcctcac cgtcctgcac    1020
caggactggc tgaatggcaa ggagtacaag tgcaaggtct ccaacaaagc cctcccagcc    1080
```

```
cccatcgaga aaaccatctc caaagccaaa gggcagcccc gagaaccaca ggtgtacacc    1140
ctgcccccat cccgggatga gctgaccaag aaccaggtca gcctgacctg cctggtcaaa    1200
ggcttctatc ccagcgacat cgccgtggag tgggagagca atgggcagcc ggagaacaac    1260
tacaagacca cgcctcccgt gctggactcc gacggctcct tcttcctcta cagcaagctc    1320
accgtggaca agagcaggtg gcagcagggg aacgtcttct catgctccgt gatgcatgag    1380
gctctgcaca accactacac gcagaagagc ctctccctgt ctccgggtaa atga          1434
```

<210> SEQ ID NO 7
<211> LENGTH: 20
<212> TYPE: PRT
<213> ORGANISM: Mus musculus

<400> SEQUENCE: 7

```
Met Glu Thr Asp Thr Leu Leu Leu Trp Val Leu Leu Leu Trp Val Pro
1               5                   10                  15

Gly Ser Thr Gly
            20
```

<210> SEQ ID NO 8
<211> LENGTH: 60
<212> TYPE: DNA
<213> ORGANISM: Mus musculus

<400> SEQUENCE: 8

```
atggagacag acacactcct gctatgggta ctgctgctct ggttccagg ttccactggt     60
```

<210> SEQ ID NO 9
<211> LENGTH: 43
<212> TYPE: DNA
<213> ORGANISM: Artificial
<220> FEATURE:
<223> OTHER INFORMATION: Synthetic Primer

<400> SEQUENCE: 9

```
gaggaaggat ctcgagctca agcttgatat cgccgccacc atg                      43
```

<210> SEQ ID NO 10
<211> LENGTH: 59
<212> TYPE: DNA
<213> ORGANISM: Artificial
<220> FEATURE:
<223> OTHER INFORMATION: Synthetic Primer

<400> SEQUENCE: 10

```
caattgatat cgccgccacc atggagacag acacactcct gctatgggta ctgctgctc     59
```

<210> SEQ ID NO 11
<211> LENGTH: 59
<212> TYPE: DNA
<213> ORGANISM: Artificial
<220> FEATURE:
<223> OTHER INFORMATION: Synthetic Primer

<400> SEQUENCE: 11

```
tgctatgggt actgctgctc tggttccag gttccactgg tgagctcgtg atgacacag      59
```

<210> SEQ ID NO 12
<211> LENGTH: 52
<212> TYPE: DNA
<213> ORGANISM: Artificial
<220> FEATURE:

<223> OTHER INFORMATION: Synthetic Primer

<400> SEQUENCE: 12
cttatcatgt ctggatcgaa gcttaattaa ctaacactct cccctgttga ag          52

<210> SEQ ID NO 13
<211> LENGTH: 43
<212> TYPE: DNA
<213> ORGANISM: Artificial
<220> FEATURE:
<223> OTHER INFORMATION: Synthetic Primer

<400> SEQUENCE: 13
cccgaggagg aacggttccg ggccgcctag ggccgccacc atg                    43

<210> SEQ ID NO 14
<211> LENGTH: 59
<212> TYPE: DNA
<213> ORGANISM: Artificial
<220> FEATURE:
<223> OTHER INFORMATION: Synthetic Primer

<400> SEQUENCE: 14
caattcctag ggccgccacc atggagacag acacactcct gctatgggta ctgctgctc   59

<210> SEQ ID NO 15
<211> LENGTH: 59
<212> TYPE: DNA
<213> ORGANISM: Artificial
<220> FEATURE:
<223> OTHER INFORMATION: Synthetic Primer

<400> SEQUENCE: 15
tgctatgggt actgctgctc tgggttccag gttccactgg tgaggtgcag ctgctcgag   59

<210> SEQ ID NO 16
<211> LENGTH: 55
<212> TYPE: DNA
<213> ORGANISM: Artificial
<220> FEATURE:
<223> OTHER INFORMATION: Synthetic Primer

<400> SEQUENCE: 16
catagagtat aatatagagt atacacctgc aggtcattta cccggagaca gggag       55

<210> SEQ ID NO 17
<211> LENGTH: 43
<212> TYPE: DNA
<213> ORGANISM: Artificial
<220> FEATURE:
<223> OTHER INFORMATION: Synthetic Primer

<400> SEQUENCE: 17
cccgaggagg aacggttccg ggccgcctag ggccgccacc atg                    43

<210> SEQ ID NO 18
<211> LENGTH: 59
<212> TYPE: DNA
<213> ORGANISM: Artificial
<220> FEATURE:
<223> OTHER INFORMATION: Synthetic Primer

<400> SEQUENCE: 18
caattcctag ggccgccacc atggagacag acacactcct gctatgggta ctgctgctc   59

```
<210> SEQ ID NO 19
<211> LENGTH: 59
<212> TYPE: DNA
<213> ORGANISM: Artificial
<220> FEATURE:
<223> OTHER INFORMATION: Synthetic Primer

<400> SEQUENCE: 19
gctatgggta ctgctgctct gggttccagg ttccactggt gatatcaaac tgcagcagt         59

<210> SEQ ID NO 20
<211> LENGTH: 55
<212> TYPE: DNA
<213> ORGANISM: Artificial
<220> FEATURE:
<223> OTHER INFORMATION: Synthetic Primer

<400> SEQUENCE: 20
catagagtat aatatagagt atacacctgc aggtcattta cccggagaca gggag             55
```

CONSTRUCTION AND APPLICATION OF BISPECIFIC ANTIBODY EPCAM×CD3

TECHNICAL FIELD

The present invention relates to the technical field of immunology, in particular to construction and a preparation method of a bispecific antibody, as well as a detection method for functions and properties of the bispecific antibody.

BACKGROUND ART

The bispecific antibody (BiAb) is an artificial antibody containing two specific antigen binding sites and can build a bridge between a target cell and a functional molecule (cell) to generate an oriented effector function. The BiAb has a broad application prospect in the biomedicine, especially in immunotherapy of tumors. To kill tumor cells through the BiAb-mediated cytotoxic effect is a hotspot of current application research of immunotherapy, and its principal characteristic lies in that the BiAb can simultaneously bind to a tumor-associated antigen and a target molecule on an immunologic effector cell and directly trigger the specific killing effect of the immunologic effector cell on the tumor cell. However, numerous obstacles, such as difficulty in expression, low yield, difficulty in purification and poor stability generally exist in the research and development process of the bispecific antibody drugs, and therefore, it is very necessary to construct a novel bispecific antibody for overcoming the barriers forementioned and construct a corresponding immunity killing animal model. The present invention provides the construction of the novel bispecific antibody and describes its pharmacological research method and result Immune cell antigens and tumor cell antigens under study and some background arts of related technology development will be introduced below.

1. CD3

The CD3 module consists of four subunits δ, ε, γ and ζ of which the molecular masses are 18.9 kDa, 23.1 kDa, 20.5 kDa and 18.7 kDa respectively and which have 171, 207, 182 and 164 amino acid residues in the length direction respectively. All the subunits constitute six peptide chains which tightly bind to a T cell receptor (TCR) usually to form a TCR-CD3 complex containing eight peptide chains (as shown in structural schematic diagram 1). This complex has the functions of transducing a T cell activation signal and stabilizing a TCR structure. The cytoplasmic domain of CD3 contains immunoreceptor tyrosine-based activation motif (ITAM), and the TCR identifies and binds to an antigen peptide presented by an MHC (major histo-compatibility complex) molecule, resulting in that a tyrosine residue in a conserved sequence of the ITAM of CD3 is phosphorylated by tyrosine protein kinase p56lck in a T cell and then other tyrosine protein kinases (such as ZAP-70) containing SH2 (Scr homology 2) structural domains can be collected. The phosphorylation of ITAM and the binding to ZAP-70 are one of important biochemical reactions in the early stage of the T cell activation signal transduction process. Therefore, the CD3 molecule has the function of transducing the activation signal generated when the TCR recognizes antigens.

2. EpCAM

The EpCAM (CD326) as a specific cell adhesion molecule of an epithelial cell is type I transmembrane glycoprotein. It also refers to some other processes, including cell migration, proliferation, differentiation and the like. EpCAM is one of earliest tumor-associated antigens which are identified by applying a monoclonal antibody technology, is widely expressed onto the epithelial tissue surface in a polymer form, mediates a Ca independent intercellular homotypic adhesion function, and can thus be classified into an adhesion molecule family. EpCAM also has other features of the adhesion molecule family and participates in multiple processes, including interaction and migration of cells and ground substances, cell differentiation, form and cell cycle regulation, signal transduction, metabolization and the like. In the meantime, EpCAM is over-expressed in multiple epithelium-derived tumors, which means that EpCAM is closely related to tumors. In a pathological circumstance, EpCAM is expressed in glandular cancers, including colorectal cancer, gastric adenocarcinoma, breast cancer, ovarian cancer, adenocarcinoma of lung, prostate cancer, pancreatic cancer, hepatocellular carcinoma and retinoblastoma in different degrees. Multiple researches have proved that the expression of EpCAM is related to proliferation, cycle distribution and metastasis of breast cancer and colonic cancer cells (as shown in Table 1). A mono-specific anti-EpCAM monoclonal antibody (MAB), such as a monoclonal antibody 17-1A (glaxowellcome, Centocor) is the first adjuvant therapy approving German EpCAM targeted therapy of colorectal cancer, however, a large amount of clinical medication data displayed that this mono-specific antibody had no remarkable and more beneficial effect compared with chemotherapy. At present, some other EpCAM targeted therapies, including bispecific antibodies, are of a growing trend for cancer therapy, and both the bispecific antibodies MT110 and Catumaxomab are therapeutic bispecific antibody drugs against tumor antigen EpCAM, wherein Catumaxomab has been approved for treating malignant cancer ascites by European Union, and MT110 has been applied in clinical researches. It was obvious that EpCAM had become one of hotshot targets for tumor therapy research at present.

TABLE 1

Extensive Distribution of EpCAM in Tumors

| Tumors | Positive Rate of EpCAM |
|---|---|
| Ovarian Cancer | 88-100% |
| Gastric Cancer | 98% |
| Colorectal Cancer | 99% |
| Pancreatic Cancer | 96% |
| Breast Cancer | 90% |
| Endometrial Cancer | 91-96% |
| Lung Cancer | 87% |
| Prostate Cancer | 98% |

3. Technological Development of Bispecific Antibody

The bispecific antibody is an antibody in which two antigen binding sites in one antibody molecule can bind to two different epitopes respectively.

The antibody drug refers to a biomacromolecular drug prepared by an antibody engineering technology taking a cell engineering technology and a genetic engineering technology as main bodies and has the advantages of high specificity, uniform property, capability of realizing directional preparation against specific targets, etc. The monoclonal antibody is mainly applied to the following three aspects in clinical practice: oncotherapy, therapy of immune diseases and anti-infective therapy. Wherein, the oncotherapy is the most extensive field for monoclonal antibody application at present, and products for oncotherapy in monoclonal antibody products that have entered clinical trial and listed in the market account for about 50%. The oncotherapy by monoclonal antibodies is an immunotherapy for killing target cells by stimulating the immune system through binding to specific targets of pathological cells, in order to enhance the effector function of the antibody, and especially the effect of killing tumor cells, and as concerned in multiple methods that have been tried by people to transform antibody molecules, the bispecific body has been one of the development trends for improving the antibody therapy effect and has become the hotspot in the field of antibody engineering researches.

The bispecific antibody for immunotherapy is an artificial antibody containing two kinds of specific antigen binding sites, is capable of building a bridge between the target cell and the functional molecule (cell) and stimulating oriented immunoreaction and has a wide application prospect in immunotherapy of tumors.

4. Preparation of Bispecific Antibody

The bispecific antibody can be obtained by multiple paths, and its preparation methods mainly include a chemical coupling method, a hybrid-hybridoma technique and a genetically engineered antibody preparation method. As concerned in the chemical coupling method, two different monoclonal antibodies are connected together in a chemical coupling manner to prepare a bispecific monoclonal antibody, which is the earliest bispecific monoclonal antibody concept, and the shortcomings of this preparation method are obvious. As concerned in the hybrid-hybridoma technique, the bispecific monoclonal antibody is produced by a cell hybridization method or a ternary hybridoma manner, and these cell hybridomas or ternary hybridomas are obtained through fusion of built hybridomas, or the fusion of the built hybridomas and mouse-derived lymphocytes, could only produce a mouse-derived bispecific antibody, and are thus limited to a great extent in application. With the rapid development of the molecular biological technology, multiple construction modes of humanized bispecific antibodies in genetic engineering have arisen, which are mainly classified into four categories, namely a bispecific micro-antibody, a double-chain antibody, a single-chain bivalent antibody and a multivalent bispecific antibody. At present, there have been several international genetically engineered bispecific antibody drugs that have been entered the clinical trial stage with a better application prospect.

5. Adoptive Immunotherapy of Tumors

As concerned in the adoptive immunotherapy of tumors, mainly comprising immunotherapy of LAK cells, TIL cells, activated T lymphocyte and CIK cells, autologous or allogeneic immunocompetent cells are delivered into the body of a patient after in vitro amplification to directly kill tumor cells, and regulate and enhance the immune function of the organism. However, the immunotherapy can be only used to remove a small number of scattered tumor cells and has a very limited effect on end-stage solid tumors, and is thus usually used as an adjuvant therapy to be combined with conventional methods, such as surgery, chemotherapy and radiotherapy. After a large number of tumor cells are cleared up by the conventional methods, residual tumor cells are removed by the immunotherapy, so that the comprehensive therapy effect on tumors can be improved. Wherein, as a new method for comprehensive therapy of tumors, the adoptive immunotherapy has been widely matched with conventional surgery, radiotherapy, chemotherapy and other cell and molecule therapies and holds great promise in therapy of multiple tumors. However, it should be a more ideal method that one end of the bispecific antibody can bind to a surface antigen CD3 of a cultured immune cell and is delivered into the body along with it, and the other end of the bispecific antibody can well bind to the surface antigen of the tumor cell; and therefore, the bispecific antibody can build a bridge between the tumor cell and the immune cell in the body, so that the immune cells are gathered around the tumor cells to further kill the tumor cells. By this method, the metastasis and diffusion of the tumor cells can be effectively solved, and the defects, such as 'halfway, easy metastasis and large side effect' in the three traditional therapy modes, namely surgery, radiotherapy and chemotherapy are overcome.

SUMMARY OF THE INVENTION

Terms and Abbreviations
BiAb: bispecific antibody
TA: tumor antigen
VH: heavy chain variable region
VL: light chain variable region
CL: constant region of light chain
CDR: Complementarity determining regions (CDRs)
ScFv: single-chain variable fragment
CLD: cell line development
FACS: fluorescence-activated cell sorting As concerned in the present invention, the construction of the new molecule—the bispecific antibody is implemented through genetic engineering and antibody engineering methods against the shortcomings of the conventional monoclonal antibodies, the T cell-mediated immunotherapy is increased for the traditional monoclonal antibodies on the basis of killing the tumor cells mainly by means of CDC, ADCC and apoptosis ability, and thus the effect of killing the tumor cells by the immune system is greatly improved.

Concretely, the present invention provides the following technical solutions:

in one embodiment, a bispecific antibody is provided, which is characterized in that it comprises: (a) a monovalent unit which is a light chain-heavy chain pair having a specific binding capability against surface antigens of the tumor cells, preferably EpCAM, CD20, CD30 and CD133, and more preferably EpCAM; and (b) a single-chain unit which is a fusion peptide comprising a single-chain variable fragment ScFv and an Fc fragment having a hinge region, a CH2 structural domain and a CH3 structural domain, wherein the immune cell directed to the fusion peptide is selected from a T cell, an NKT cell or a CIK cell; and preferably, the fusion peptide has a specific binding capability against the surface antigen CD3 of the immune cell.

In one embodiment, the CH2 structural domain of the single-chain unit of the bispecific antibody is positioned between the ScFv fragment and the CH3 structural domain; and the single-chain unit does not contain a CH1 structural domain.

In one embodiment, the single-chain variable fragment of the bispecific antibody consists of a light chain variable region structural domain and a heavy chain variable region structural domain, both of which are targeted to the antigen epitope CD3.

In one embodiment, in the monovalent unit, both the light-chain constant region structural domain and the light-chain variable region structural domain of the light chain are targeted to the tumor antigen epitope EpCAM; both the heavy-chain constant structural domain CH1 and the heavy-chain variable structural domain of the heavy chain are targeted to the tumor antigen epitope EpCAM; the light chain binds to the heavy chain through a disulfide bond; and the heavy chain binds to the fusion peptide through one or more disulfide bonds.

In one embodiment, the single-chain unit comprises an anti-CD3 antibody directed to CD3, wherein the monovalent unit comprises an anti-EpCAM antibody directed to EpCAM.

In one embodiment, the amino acid sequence of a heavy chain of the anti-EpCAM antibody is the amino acid sequence as shown in SEQ ID NO. 1, the amino acid sequence of a light chain of the anti-EpCAM antibody is the amino acid sequence as shown in SEQ ID NO. 3 and the amino acid sequence of the ScFv-Fc of the anti-CD3 antibody is the amino acid sequence as shown in SEQ ID NO. 5; in addition, cysteine of the heavy chain of the anti-EpCAM antibody on the site 223 is connected with cysteine of the light chain of the anti-EpCAM antibody on the site 220 in a manner of disulfide bonds, cysteines of the heavy chain of the anti-EpCAM antibody on sites 229 and 232 are connected with cysteines of the ScFv-Fc of the anti-CD3 antibody on sites 255 and 258 respectively in a manner of disulfide bonds, the sites 395 and 412 in the heavy chain of the anti-EpCAM antibody are in salt bridge connection with sites 428 and 397 of the ScFv-Fv of the anti-CD3 antibody, and the site 369 in the heavy chain of the anti-EpCAM antibody is in hump-indent-cavity connection with the site 436 of the ScFv-Fc of the anti-CD3 antibody.

In one embodiment, the heavy chain in the monovalent unit contains a human or humanized Fc fragment, preferably, the Fc fragment of the heavy chain comprises a human IgG Fe fragment; and an Fc fragment of the fusion peptide contains a human or humanized Fc fragment, preferably the Fc fragment of the fusion peptide comprises a human IgG Fc fragment.

In one embodiment, both the human IgG Fe fragment of the monovalent unit and the IgG Fc fragment of the single-chain unit are connected through a salt bridge and a hump-indent-cavity structure.

In one embodiment, the preparation method of the bispecific antibody is provided, comprising:

(1) establishing a heavy chain and a light chain of the monovalent unit to a first expression vector respectively and establishing a single-chain unit to a second expression vector;

(2) co-transfecting the first expression vector and the second expression vector to a cell, culturing and taking supernatant; and (3) separating the expression supernatant to obtain a purified bispecific antibody; preferably, said cell is a CHO-S cell; or preferably, the separation step comprises: capturing all antibodies with Fc structural domains from the expression supernatant through a protein A affinity column, separating the target bispecific antibody from byproducts through SP cation exchange chromatography, then passing a Q column and finally concentrating and displacing a buffer solution PBS.

In one embodiment, the first expression vector is pCHO1.0; the second expression vector is pCHO1.0-hygromycin.

In one embodiment, the monovalent unit is an anti-EPCAM antibody, primers used for amplifying the light chain of said antibody are Kozak(EcoRV)F, MK-leader sequence (EcoRV)F, M701-VL F1 and hIgK (PacI)R, and the Kozak sequence, the leader sequence and restriction enzyme cutting sites EcoRV and Pad are introduced to the light chain through overlap PCR amplification; primers used for amplifying the heavy chain of said antibody are Kozak (AvrII)F, MK-leader sequence (AvrII)F, M701-VH F1 and hIgG1(sbfI)R, and the Kozak sequence, the leader sequence and restriction enzyme cutting sites AvrII and BstZ17I are introduced to the heavy chain through overlap PCR amplification; the amplified LC gene fragment is subject to homologous recombination with the pCHO1.0 expression vector suffering restriction enzyme cutting via EcoRV and PacI to obtain an anti-EpCAM light chain-loaded expression vector and is then subject to homologous recombination with HC after suffering restriction enzyme cutting via AvrII and BstZ17I to obtain an anti-EpCAM pCHO1.0 expression vector of which the plasmid is named as pCHO1.0-anti-EpCAM-HL-KKW.

The single-chain unit is an anti-CD3 ScFv-Fv antibody, primers used for amplifying said antibody are Kozak(AvrII)F, MK-leader sequence (AvrII)F, L2K-VH(MK)F1 and hIgG1 (sbfI)R, and the anti-CD3 ScFv-Fc-loaded expression vector of which the plasmid is named as pCHO1.0-hygromycin-L2K-ScFv-Fc-LDY is obtained through implementing overlap PCR amplification of an anti-CD3 ScFv-Fc structural domain, introducing the Kozak sequence, the lead sequence and restriction enzyme cutting sites AvrII and BstZ17I into ScFv-Fc and carrying out homologous recombination on the amplified gene fragment and the pCHO1.0-hygromycin expression vector suffering restriction enzyme cutting.

In one embodiment, as concerned in any bispecific antibody and use of the bispecific antibody prepared via any method forementioned in preparing drugs, said drugs are used to treat tumors or related diseases caused by EpCAM specific antigen expression or kill cells expressing EpCAM.

In one embodiment, as concerned in any one bispecific antibody or use of the bispecific antibody prepared via any one of methods forementioned in preparing drugs, said drugs are used to screen bispecific antibody drugs for treating tumor cell-associated diseases caused by expression of EpCAM specific antigen from a tumor cell line or evaluate the efficacy of the bispecific antibody drugs for treating tumor cell-associated diseases caused by expression of EpCAM specific antigen. The present invention also provides the following technical solutions:

the present invention provides a novel antibody called as the bispecific antibody and establishes a method for carrying out immunotherapy by using an immune system of the human body and performing the pharmacological study of the bispecific antibody. As a novel antibody for a pharmacological model, this bispecific antibody introduces the specific cytotoxicity efficacy of a T cell to tumor antigens, such as EpCAM.

The present invention provides a new method for preparing the bispecific antibody MSBODY (monomer and ScFv bispecific antibody) as shown in FIG. 2. The bispecific antibody comprises two groups of heavy and light chain combinations, wherein one group specifically binds to one kind of antigen, is subject to some transformations on its heavy chain Fc region, and is thus not easy to form a dimer per se relative to a wild type; whereas, the other group specifically binds to another kind of antigen, is subject to some other transformations on its heavy chain Fc region and is thus also not easy to form a dimer per se, and moreover, a hybrid dimer is easy to form between the two groups of heavy and light chains. In addition, the antibody structure of one of the two groups is a unimer Ab and the other group is a ScFv-Fc, so that the possibility that respective light chain and the heavy chain of the opposite side are mismatched is avoided, and thus a bispecific antibody protein molecule of 125KD is formed. After Fc transformation, the heavy chain and the single chain of the unimer Ab are naturally iso-dimerized, and meanwhile, CL and CH1 are naturally dimerized to finally form the MSBODY, and the arrangement sequence of various structural domains and the structural schematic diagram of the MSBODY are as shown in FIG. 2.

According to the method for preparing the bispecific antibody as disclosed in the present invention, the bispecific antibody is prepared. Wherein, the bispecific antibody taking EpCAM and CD3 as targets is named as EpCAM×CD3, and as shown in FIG. 2, the anti-EPCAM side is of an IgG form and comprises an anti-EPCAM heavy chain and light chain, whereas the anti-CD3 side is of a ScFv-Fc form and comprises anti-CD3 VH, VL and Fc structural domains. The bispecific antibody forementioned is established through an antibody genetic engineering method, and the bispecific antibody MSBODY involves a unimer Ab heavy chain and unimer Ab light chain binary expression vector and a ScFv-Fc expression vector. Primers are designed according to LC, HC, ScFv, Fc gene sequences and multiple cloning sites in the vectors. Wherein, PCR amplification is implemented respectively for LC, HC, ScFv and Fc, and a gene fragment is obtained via PCR or overlap extension by PCR and is then cloned via a homologous recombination method. The pCHO1.0 or pCHO1.0-hygromycin vector is subject to restriction enzyme cutting and then a PCR product and vectors suffering restriction enzyme cutting are purified and recovered, the LC fragment and the HC fragment are cloned onto the pCHO1.0 vector in a homologous recombination manner by two steps, and the ScFv-Fc fragment is cloned onto the pCHO1.0-hygromycin vector in a homologous recombination manner and is then sequenced. According to the expression and detection of the recombinant protein MSBODY in mammalian cells, two kinds of plasmids expressing the unimer Ab heavy chain, the unimer Ab light chain and a single chain respectively are co-transfected to the mammalian cells by using a transfection reagent, and then supernatant is collected and undergoes SDS-PAGE and western blotting, to detect the expression condition of the MSBODY. The supernatant of the culture solution subject to transfection expression is centrifuged and filtered, is then diluted with a binding buffer solution, passes through an affinity column, is eluted with an elution buffer solution, and is subject to SDS-PAGE detection to purify the protein.

The invention also provides a method for tumor model construction and pharmacological detection. The pharmacological model construction and the pharmacological detection mainly lie in that a humanized tumor stable cell line expressing humanized EpCAM and human CIK cells subject to isolated culture are mixed to efficiently form tumors in mice with immunodeficiency and are medicated by utilizing the constructed bispecific antibody which can simultaneously bind to a tumor cell, a T cell expressing CD3 and an immune accessory cell capable of binding to Fc, so that a bridge is built between the immune cell and the tumor cell to form an immune complex, and the immune cell generates a violent immune reaction to secrete multiple cell factors for killing the tumor cells, and thus inhibiting the growth of the tumors. This model is developed in a simulated immune system, is used for killing the tumors by using immune cells, is capable of effectively reflecting the pharmacological effect of the bispecific antibody-medicated immune cells for killing the tumor cells and provides a favorable pharmacological estimation method for development of bispecific antibody drugs targeting the immune cells and the tumor cells.

The technical solution of the present invention has the beneficial effects:

1. the present invention discloses construction of the novel bispecific antibody MSBODY as well as establishment and its application of an animal model of killing tumor cells by the novel bispecific antibody MSBODY-mediated immune cells. The present invention includes preparation of an immune cell-killing bispecific antibody mediated in the bispecific antibody drug research process, as well as establishment and detection of a bispecific antibody pharmacological model. The bispecific antibody MOBODY comprises a group of heavy and light chain combination, and the other group of ScFv-binding Fc combination, wherein one group specifically binds to a kind of human tumor cell antigens comprising a series of tumor cell membrane surface antigens, such as EpCAM, and is subject to some transformations in its heavy chain Fc region, and is thus not easy to form a dimer per se relative to the wild type; whereas, the other group specifically binds to another mouse-derived T cell antigen CD3, is subject to some transformations in its heavy chain Fc region as well, and is thus also not easy to form a dimer per se, and moreover, a heterodimer is easy to form between the two groups of heavy chains and light chains. In the meantime, the bispecific antibody can build a bridge between the target cell and the functional molecule (cell) to stimulate the oriented immunoreaction. In the presence of immune cells, the bispecific antibody as disclosed in the present invention has an extremely strong killing effect on tumor cells and thus has a wide application prospect in immunotherapy of tumors.

2. The present application provides a heterodimer antibody comprising two different antigen-binding polypeptide units. The heterodimer and its corresponding homodimer are different in molecular weight and can be distinguished according to the molecular weight, and therefore, the purity of the bispecific antibody can be determined effectively. One of the two antigen-binding polypeptide units comprises a light chain-heavy chain pair similar to that of a wild type antibody and is also called as a 'monovalent unit' in the whole present application. The other antigen-binding polypeptide unit comprises a single-chain variable fragment (ScFv). So, the ScFv can be fused to a constant fragment (Fc) of the antibody. The fusion peptide in the full text of the present application is also called as a 'single-chain unit'.

What is surprising, the present application has proved that this unsymmetrical antibody is stable and has high antigen binding efficiency, which is unexpected since it has been proved that even the homodimer of the single-chain antibody is instable under the physiological condition. For instance, 'ScFv Antibody: Principles and Clinical Application,' (Clinical and Developmental Immunology, 2012: 980250(2012)) of Ahmad, et al, displayed that ScFv-based IgG antibodies are instable and need to be further transformed so as to reduce the aggregation and improve the stability.

In addition, because of having asymmetry, the heterodimer has isoelectric points different from those of the homodimer consisting of any one antigen-binding polypeptide unit. Based on the isoelectric point difference between the heterodimer and the homodimer, the required heterodimer and homodimer can be separated easily, and thus the difficulty in downstream technique development generally existing in the bispecific antibodies is greatly reduced.

BRIEF DESCRIPTION OF THE DRAWINGS

Drawings that need to be used in the examples will be briefly introduced below in order to illustrate the technical solution in the examples of the present application more clearly, and it is apparent for those common skilled in the art that the drawings described as below are just some examples recorded in the present invention and other drawings can also be acquired on the basis of those drawings on the premise of not paying creative work, wherein.

SPECIFIC MODES FOR CARRYING OUT THE INVENTION

The present invention will be further described in detail bellow in conjunction with the specific examples and by reference to the drawings. It should be understood that the examples in the description are just for the purpose of illustrating the present invention, but not limiting the scope of the present invention in any way.

EXAMPLE 1

Construction of Expression Vector of Bispecific Antibody (EpCAM×CD3, M701)

1. Sequence Design of Bispecific Antibody

Figure 1:
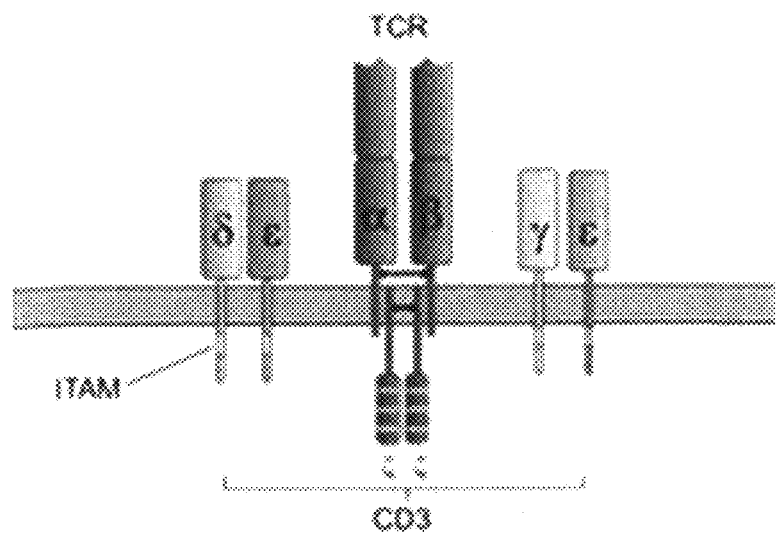
FIG. 1 is a structural schematic diagram of the CD3 molecule.
Figure 2:
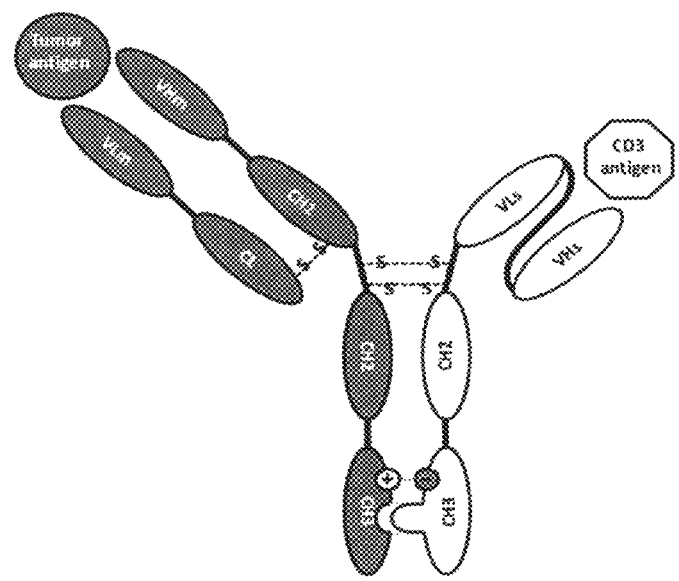
FIG. 2 is a schematic diagram of the EpCAM×CD3 bispecific antibody molecule.

The bispecific antibody taking EpCAM and CD3 as targets is named as M701 (as shown in FIG. 2), wherein the anti-EpCAM side is of an IgG form, includes anti-EpCAM heavy chain and light chain and contains Fab and Fc structural domains; the anti-CD3 side is of an ScFv-Fc form and comprises anti-CD3 VH, VL and Fc structural domains. Wherein, Fc of the side of the IgG form is subject to KKW transformation, whereas Fc of the ScFv-Fc side is subject to LDY transformation (the specific Fc transformation process refers to PCT/CN2012/084982), so that each of which is not easy to form a homodimer, but is easy to form a heterodimer, namely the EpCAM×CD3 bispecific antibody. In the meantime, in order to ensure that the bispecific antibody can be expressed in a CHO cell and secreted into a culture medium, a leading peptide sequence of a mouse-derived kappa chain is selected as a secretary signal peptide. The amino acid sequences and the nucleotide sequences of all structural domains and the signal peptide are as shown in SEQ ID No. 1-8.

Anti-EpCAM Heavy Chain
(Amino Acid Sequence SEQ ID NO. 1)
EVQLLEQSGAELVRPGTSVKISCKASGYAFTNYWLGWVKQRPGHGLEWIGDIFPGSGNI

HYNEKFKGKATLTADKSSSTAYMQLSSLTFEDSAVYFCARLRNWDEPMDYWGQGTTV

TVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSRDELTKNQVSLWCLVKGFYPSDIAVEWESNGQPENNYDTTPPVLDSDGSFFLYSD

LTVDKSRWQQGNVFSCSVMHEALHNHYTQKSLSLSPGK

Anti-EpCAM Heavy Chain
(Nucleotide Sequence SEQ ID NO. 1)
GAGGTGCAGCTGCTCGAGCAGTCTGGAGCTGAGCTGGTAAGGCCTGGGACTTCA

GTGAAGATATCCTGCAAGGCTTCTGGATACGCCTTCACTAACTACTGGCTAGGTTG

GGTAAAGCAGAGGCCTGGACATGGACTTGAGTGGATTGGAGATATTTTCCCTGGA

AGTGGTAATATCCACTACAATGAGAAGTTCAAGGGCAAAGCCACACTGACTGCAG

ACAAATCTTCGAGCACAGCCTATATGCAGCTCAGTAGCCTGACATTTGAGGACTCT

GCTGTCTATTTCTGTGCAAGACTGAGGAACTGGGACGAGCCTATGGACTACTGGG

GCCAAGGGACCACGGTCACCGTCTCCTCCGCGTCGACCAAGGGCCCATCGGTCTT

CCCCCTGGCACCCTCCTCCAAGAGCACCTCTGGGGGCACAGCGGCCCTGGGCTGC

CTGGTCAAGGACTACTTCCCCGAACCGGTGACGGTGTCGTGGAACTCAGGCGCCC

TGACCAGCGGCGTGCACACCTTCCCGGCTGTCCTACAGTCCTCAGGACTCTACTC

CCTCAGCAGCGTGGTGACCGTGCCCTCCAGCAGCTTGGGCACCCAGACCTACATC

TGCAACGTGAATCACAAGCCCAGCAACACCAAGGTGGACAAGAAAGTTGAGCCC

AAATCTTGTGACAAAACTCACACATGCCCACCGTGCCCAGCACCTGAACTCCTGG

GGGGACCGTCAGTCTTCCTCTTCCCCCCAAAACCCAAGGACACCCTCATGATCTC

CCGGACCCCTGAGGTCACATGCGTGGTGGTGGACGTGAGCCACGAAGACCCTGA

GGTCAAGTTCAACTGGTACGTGGACGGCGTGGAGGTGCATAATGCCAAGACAAA

GCCGCGGGAGGAGCAGTACAACAGCACGTACCGTGTGGTCAGCGTCCTCACCGT

CCTGCACCAGGACTGGCTGAATGGCAAGGAGTACAAGTGCAAGGTCTCCAACAA

AGCCCTCCCAGCCCCCATCGAGAAAACCATCTCCAAAGCCAAAGGGCAGCCCCG

AGAACCACAGGTCTACACCCTGCCCCCATCCCGGGATGAGCTGACCAAGAACCAG

GTCAGCCTGTGGTGCCTGGTCAAAGGCTTCTATCCCAGCGACATCGCCGTGGAGT

GGGAGAGCAATGGGCAGCCGGAGAACAACTACGATACCACGCCTCCCGTGCTGG

ACTCCGACGGCTCCTTCTTCCTCTACAGCGATCTCACCGTGGACAAGAGCAGGTG

GCAGCAGGGGAACGTCTTCTCATGCTCCGTGATGCATGAGGCTCTGCACAACCAC

TACACGCAGAAGAGCCTCTCCCTGTCTCCGGGTAAATGA

Anti-EpCAM Light Chain
(Amino Acid Sequence SEQ ID NO. 3)
ELVMTQSPSSLTVTAGEKVTMSCKSSQSLLNSGNQKNYLTWYQQKPGQPPKLLIYWAS

TRESGVPDRFTGSGSGTDFTLTISSVQAEDLAVYYCQNDYSYPLTFGAGTKLEIKRTVAA

PSVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

-continued

Anti-EpCAM Light Chain
(Nucleotide Sequence SEQ ID NO. 4)
GAGCTCGTGATGACACAGTCTCCATCCTCCCTGACTGTGACAGCAGGAGAGAAGG

TCACTATGAGCTGCAAGTCCAGTCAGAGTCTGTTAAACAGTGGAAATCAAAAGAA

CTACTTGACCTGGTACCAGCAGAAACCAGGGCAGCCTCCTAAACTGTTGATCTAC

TGGGCATCCACTAGGGAATCTGGGGTCCCTGATCGCTTCACAGGCAGTGGATCTG

GAACAGATTTCACTCTCACCATCAGCAGTGTGCAGGCTGAAGACCTGGCAGTTTA

TTACTGTCAGAATGATTATAGTTATCCGCTCACGTTCGGTGCTGGGACCAAGCTTG

AGATCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAG

AGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACC

CTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGT

TAG

Anti-CD3 ScFv-Fc
(Amino Acid Sequence SEQ ID NO. 5)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSGGGGSGGGGSGGGGSQIVLTQSPAIMSASPG

EKVTMTCSASSSVSYMNWYQQKSGTSPKRWIYDTSKLASGVPAHFRGSGS

GTSYSLTISGMEAEDAATYYCQQWSSNPFTFGSGTKLEINRGAAAEPKSC

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

Anti-CD3 ScFv-Fc
(Nucleotide Sequence SEQ ID NO. 6)
CAGGTGCAGCTGGTGCAGAGCGGCGGCGGCGTCGTGCAGCCGGGCAGGTC

CCTGAGACTGTCTTGTAAGGCTTCTGGATACACCTTCACTAGATACACAA

TGCACTGGGTCAGACAGGCTCCTGGAAAGGGACTCGAGTGGATTGGATAC

ATTAATCCTAGCAGAGGTTATACTAACTACAATCAGAAGTTTAAGGACAG

ATTCACAATTTCTACTGACAAATCTAAGAGTACAGCCTTCCTGCAGATGG

ACTCACTCAGACCTGAGGATACCGGAGTCTATTTTTGTGCTAGATATTAC

GATGACCACTACTGTCTGGACTACTGGGGCCAAGGTACCCCGGTCACCGT

GAGCTCAGGAGGCGGCGGTTCAGGCGGAGGTGGAAGTGGTGGAGGAGGTT

CTGATATTCAGATGACCCAGAGCCCGTCAAGCTTATCTGCTTCTGTCGGA

GACAGAGTCACAATCACATGTTCTGCTTCTAGCTCTGTCTCTTACATGAA

CTGGTATCAGCAGACACCTGGAAAGGCTCCTAAGCGGTGGATCTACGACA

CATCTAAGCTCGCTTCTGGAGTCCCTTCTAGATTCTCTGGTTCTGGCTCT

GGAACAGACTACACATTCACAATCTCTTCTCCAACCTGAGGACATCGC

TACATACTACTGCCAACAGTGGTCTAGCAATCCTTTCACATTCGGACAGG

```
-continued
GTACCAAACTGCAGATCACAAGAGGTGCGGCCGCAGAGCCCAAATCTTGT

GACAAAACTCACACATGCCCACCGTGCCCAGCACCTGAACTCCTGGGGGG

ACCGTCAGTCTTCCTCTTCCCCCCAAAACCCAAGGACACCCTCATGATCT

CCCGGACCCCTGAGGTCACATGCGTGGTGGTGGACGTGAGCCACGAAGAC

CCTGAGGTCAAGTTCAACTGGTACGTGGACGGCGTGGAGGTGCATAATGC

CAAGACAAAGCCGCGGGAGGAGCAGTACAACAGCACGTACCGTGTGGTCA

GCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTC

CAAAGCCAAAGGGCAGCCCCGAGAACCACAGGTGTACACCCTGCCCCCAT

CCCGGGATGAGCTGACCAAGAACCAGGTCAGCCTGACCTGCCTGGTCAAA

GGCTTCTATCCCAGCGACATCGCCGTGGAGTGGGAGAGCAATGGGCAGCC

GGAGAACAACTACAAGACCACGCCTCCCGTGCTGGACTCCGACGGCTCCT

TCTTCCTCTACAGCAAGCTCACCGTGGACAAGAGCAGGTGGCAGCAGGGG

AACGTCTTCTCATGCTCCGTGATGCATGAGGCTCTGCACAACCACTACAC

GCAGAAGAGCCTCTCCCTGTCTCCGGGTAAATGA

Leading Peptide Sequence
(Amino Acid Sequence SEQ ID NO. 7)
of Mouse-Derived Kappa Chain
METDTLLLWVLLLWVPGSTG Leading Peptide Sequence
(Amino Acid Sequence SEQ ID NO. 8)
of Mouse-Derived Kappa Chain
atggagacagacacactcctgctatgggtactgctgctctgggttccaggttccactggt
```

2. Gene Cloning of Bispecific Antibody pCHO1.0 was selected as an expression vector for cloning and expressing anti-EpCAM heavy chain and light chain genes, and a pCHO1.0-hygromycin expression vector was obtained by modification through replacing a puromycin gene in a pCHO1.0 vector with a hygromycin resistant gene and was selected to clone and express the anti-CD3 ScFv-Fc fusion gene. The primers in Table 1 were delivered to GENEWIZ, Inc, Suzhou for synthesis after being designed according to a cloning solution. The primers as shown in Table 1 were subject to PCR amplification, a gene plasmid obtained from gene synthesis or subcloned to pCDNA3.1 or pUC57 in the early-stage experiment acted as a template (which was described in PCT/CN2012/084982 patent in detail), and then the anti-EpCAM heavy and light chains were established to the pCHO1.0 expression vector respectively, and the anti-CD3 ScFv-Fc was established onto the pCHO1.0-hyromycin expression vector.

TABLE 1

Primers Used in Gene Cloning of Bispecific Antibody

| Names of Fragments | Names of Primers | SEQ ID NO. | Sequences |
| --- | --- | --- | --- |
| Anti-EpCAM LC | Kozak(EcoR V)F | 9 | gaggaaggatctcgagctcaagcttgatatcgccgccaccatg |
| | MK-Leading Sequence (EcoRV)F | 10 | CAATTgatatcgccgccaccatggagacagacacactcctgctatgggtactgctgctc |
| | M701-VL F1 | 11 | tgctatgggtactgctgctctgggttccaggttccactggtgagctcgtgatgacacag |
| | hIgK (PacI)R | 12 | cttatcatgtctggatcgaagcttaattaactaacactctcccctgttgaag |
| Anti-EpCAM HC | Kozak(Avr II)F | 13 | cccgaggaggaacggttccgggccgcctagggccgccaccatg |
| | MK-Leading Sequence (AvrII)F | 14 | CAATTcctagggccgccaccatggagacagacacactcctgctatgggtactgctgctc |
| | M701-VH F1 | 15 | tgctatgggtactgctgctctgggttccaggttccactggtgaggtgcagctgctcgag |
| | hIgG1(sbfI)R | 16 | catagagtataatatagagtatacacctgcaggtcatttacccggagacagggag |

TABLE 1-continued

Primers Used in Gene Cloning of Bispecific Antibody

| Names of Fragments | Names of Primers | SEQ ID NO. | Sequences |
|---|---|---|---|
| Anti-CD3 ScFv-Fc | Kozak(Avr II)F | 17 | cccgaggaggaacggttccgggccgcctagggccgccaccatg |
| | MK-Leading Sequence (AvrII)F | 18 | CAATTcctagggccgccaccatggagacagacacactcctgctat gggtactgctgctc |
| | L2K-VH(MK)F1 | 19 | gctatgggtactgctgctctggttccaggttccactggtgatatcaaac tgcagcagt |
| | hIgG1(sbfI)R | 20 | catagagtataatatagagtatacacctgcaggtcatttacccggagac agggag |

Initial PCR amplification template DNA: 35 ng template DNA, such as a light chain and a heavy chain of a target antibody; 1 μl of 10 μM forward primer and reverse primer; 2.5 μl of 10×PCR Buffer solution; 1 μl of 10 mM dNTP; 1 μl of 2.5 unit/μl Pyrobest DNA polymerase (Takara, R005A); and distilled water to 25 μl by total volume, all of which were softly mixed in a microfuge tube and rapidly rotated in a microcentrifuge so as to collect the reaction mixture to the bottom of the tube. PCR reaction was performed by using Gene Amp PCR System 9700 (Applied Biosystem) according to the following settings: 5 minutes at 95° C.; and 25 cycles as below: 30 seconds each time at 95° C.; 30 seconds at 56° C.; and 1 minute at 72° C.

Figure 3:
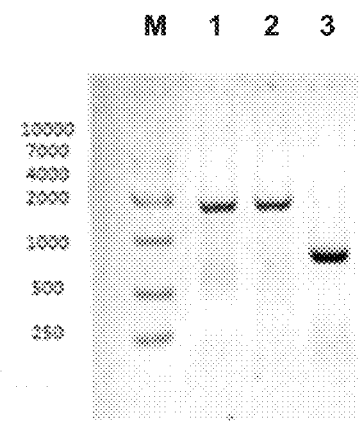
FIG. 3 is an electrophoresis detection PCR product diagram; M: DL10000 nucleic acid molecular marker; 1. Anti-CD3 antibody ScFv-Fc; 2. heavy chain of the anti-EpCAM antibody; and 3. light chain of the anti-EpCAM antibody.
Figure 4:
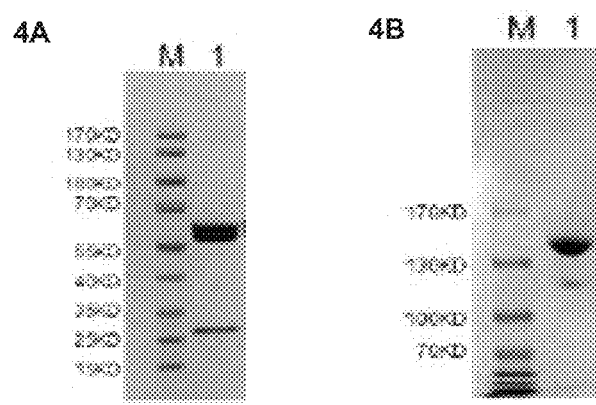
FIG. 4 is a purified bispecific antibody electrophoresis and purity detection result diagram; (4A) denatured SDS-PACE electrophoresis; M: protein molecular weight marker; 1:EpCAM×CD3 bispecific antibody; (4B) non-denatured SDS-PACE electrophoresis; M: protein molecular weight marker; 1:EpCAM×CD3 bispecific antibody; and (4C) HPLC-SEC purity peak shape diagram of EpCAM×CD3.
Figure 4:
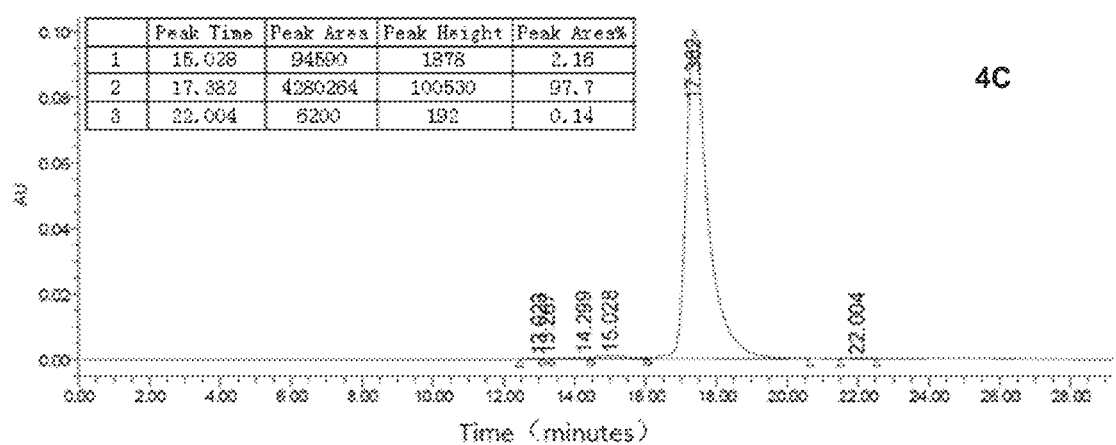

Via several cycles of overlap PCR amplification, the Kozak sequence, the leader sequence and restriction enzyme cutting sites EcoRV and PacI were introduced into the light chain (as shown in FIG. 3); and the Kozak sequence, the leader sequence and restriction enzyme cutting sites AvrII and BstZ17I were introduced into the heavy chain by the corresponding primers (as shown in FIG. 3). Firstly, the amplified LC gene fragment was subject to homologous recombination with a pCHO1.0 expression vector suffering restriction enzyme cutting via EcoRV and PacI to obtain the anti-EpCAM light chain-loaded expression vector, and was then subject to homologous recombination with HC after suffering restriction enzyme cutting via AvrII and BstZ17I to obtain the anti-EpCAM pCHO1.0 expression vector of which the plasmid is named as pCHO1.0-anti-EpCAM-HL-KKW.

The anti-CD3ScFv-Fc-loaded expression vector of which the plasmid is named as pCHO1.0-hygromycin-L2K-ScFV-Fc-LDY was obtained through implementing overlap PCR amplification of an anti-CD3ScFv-Fc structural domain, introducing the Kozak sequence, the leader sequence and restriction enzyme cutting sites AvrII and BstZ17I into ScFv-Fc and carrying out homologous recombination on the amplified gene fragment (as shown in FIG. 3) and the pCHO1.0 expression vector suffering restriction enzyme cutting.

EXAMPLE 2

Expression and Purification of Bispecific Antibody

1. Expression of Bispecific Antibody

Plasmid maxiprep was performed by using an endotoxin-free maxiprep kit (Qiagen, 12391) and specific operations were performed according to the instructions provided by the manufacturer. CHO-S cell culture was performed in a CD CHO culture medium (Gibco, 10743-029) at 37° C. in a 5% $CO_2$ cell incubator according to the instructions provided by the manufacturer, and after the cells were prepared, plasmids pCHO1.0-anti-EpCAM-HL-KKW and pCHO1.0-Herceptin-L2K-ScFv-Fc-LDY were co-transfected to the CHO-S cells by using a Maxcyte STX electroporation apparatus so as to express the bispecific antibody M701 directed to anti-EpCAM×CD3 according to the instructions (Maxcyte) provided by the manufacturer.

After the second day of co-transfection, the culture temperature drops to 32° C., 3.5% Feed A was replenished every day, and after culture for 14 days, the supernatant was harvested by 800*g centrifugal.

2. Purification of Bispecific Antibody

The expression supernatant was filtered with a 0.22 uM filter membrane, an antibody with an Fc structural domain was captured from the expression supernatant by using a Mabselect SuRe affinity column (purchased from GE Company, Column Art. No. 18-1153-45 and Filler Art. No. 17-5438-01), passed through the affinity column which was balanced with an equilibration buffer solution (9.5 mM $NaH_2PO_4$+40.5 mM $Na_2HPO_4$,pH7.0) and was eluted with an elution buffer solution (50 mM citric acid+100 mM arginine, pH3.2). The target bispecific antibody and byproducts were separated by means of SP cation exchange chromatography, wherein the cation exchange column was purchased from GE Company (Column Art. No. 18-1153-44, 17-1087-01); and after the column was balanced with an equilibration buffer solution A (43.8 mM $NaH_2PO_4$+6.2 mM $Na_2HPO_4$, pH6.0), a sample was diluted with double pure water, was electrically conducted to a range from 3.0 ms to 3.5 ms and was subject to linear elution of 20 column volumes with an elution buffer solution B (43.8 mM $NaH_2PO_4$+6.2 mM $Na_2HPO_4$+1M NaCl, pH6.0) after being combined with an SP column; and finally, Buffer PBS was concentrated and displaced. The purified bispecific antibody had the purity over 95% via SDS-PAGE and SEC detection (as shown in FIG. 3).

EXAMPLE 3

Binding Activity Measurement (FACS) of Bispecific Antibody and Cells

The bispecific antibody of the present invention binds to target antigens on the corresponding cells. As concerned in the present invention, with HCT116 (purchased from American Type Culture Collection ATCC, CCL-247) as an EpCAM positive cell and Jurkat (Jurkat, TIB-152) as a CD3 positive cell, the cell binding activity therebetween was measured by means of the bispecific antibody prepared in the present invention.

Figure 5:
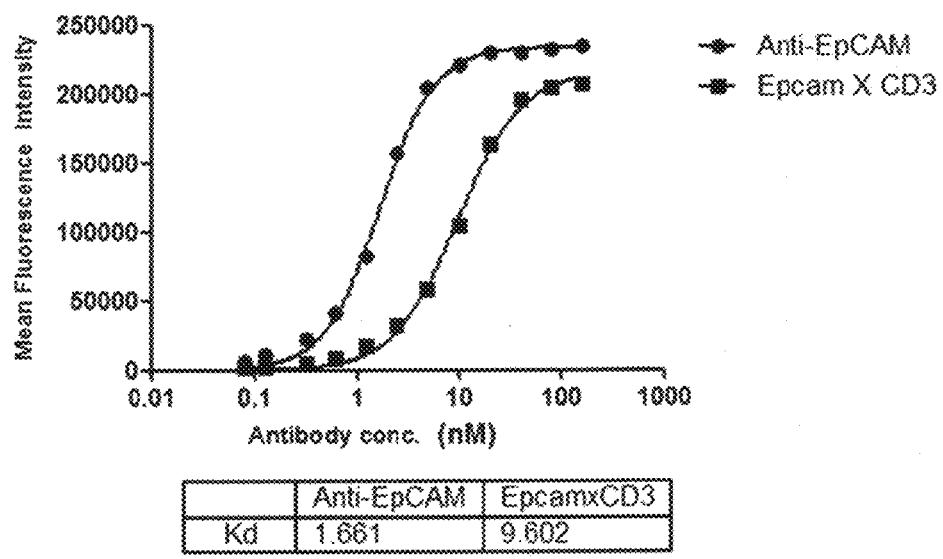
FIG. 5 is an affinity condition diagram of the EpCAM×CD3 bispecific antibody and HCT116 cells measured based on fluorescence-activated cell sorting, (■) EpCAM×CD3 MSBODY; and (●) Anti-EpCAM monoclonal antibody.

1. Detection of Binding Activity of Bispecific Antibody and the HCT116 Cells Via Fluorescence-Activated Cell Sorting Enough HCT116 cells are cultured, digested with 0.25% trypsin and then collected by centrifugation. In the meantime, the bispecific antibody was diluted according to the concentration beginning from 10 ug/ml and ten-fold gradient dilution to obtain twelve concentration gradients for later use. The collected cells are washed twice with PBS+1% FBS and resuspended to $4 \times 10^6$ cell/ml with PBS+1% FBS and plated in a 96-well plate each well of which was loaded with 50 ul ($2 \times 10^5$ cells), 50 ul of diluted bispecific antibody was added and cells were incubated for 1 hour at room temperature; and supernatant was removed by centrifugation, cells were washed twice with PBS, then resuspended with a diluted PE-marked anti-human IgG FC antibody (Biolegend, 409304), incubated for 30 minutes at room temperature in a dark place, washed twice with PBS, then resuspended with 100 ul PBS and detected on an instrument, and then, the binding affinity KD value of the bispecific antibody and the HCT116 was analyzed and calculated according to the mean fluorescence intensity by using software GraphPadPrism 5.0. The result displaysed that the EpCAM×CD3 bispecific antibody had favorable binding activity with the EpCAM-positive HCT116 cells, and as shown in FIG. 5, the KD value was 9.602 nM, the KD detection result of Anti-EpCAM was 1.661 nM.

Figure 6:
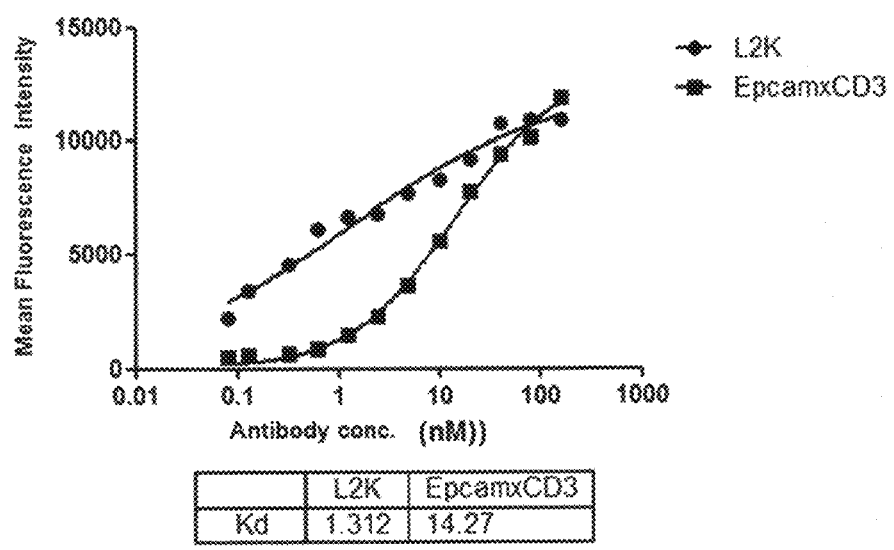
FIG. 6 is an affinity condition diagram of the EpCAM×CD3 bispecific antibody and Jurkat cells measured based on fluorescence-activated cell sorting, (■) EpCAM×CD3 MSBODY; and (●) Anti-CD3 monoclonal antibody L2K.

2. Detection of Binding Activity of the Bispecific Antibody and Jurkat Cells Via Fluorescence-Activated Cell Sorting Enough Jurkat suspension cells were cultured and collected by centrifugation. The same as the steps described in the example forementioned, in the following experimental process, the cells resuspended with 100 ul PBS were detected on an instrument, and the binding affinity KD value of the bispecific antibody and the Jurkat cells was analyzed and calculated according to the mean fluorescence intensity by using software GraphPadPrism 5.0. The result displayed that the EpCAM×CD3 bispecific antibody had favorable binding activity with the CD3-positive Jurkat cells, and as shown in FIG. 6, the KD value was 14.27 nM which displayed the favorable affinity.

Figure 7:
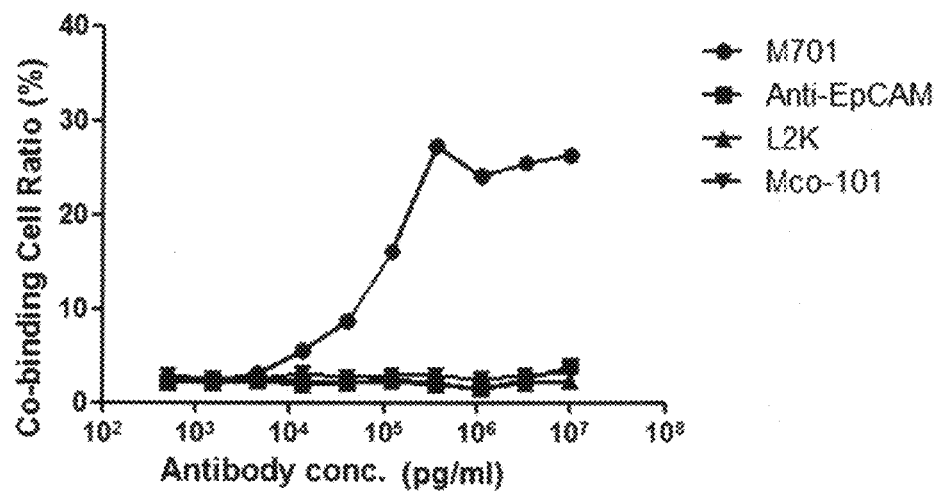
FIG. 7 is a result diagram that the EpCAM×CD3 bispecific antibody simultaneously binds to HCT116 cells and Jurkat cells in the process of flow cytometry detection and pulls the two kinds of cells together; (●) EpCAM×CD3 bispecific antibody; (■) EpCAM monoclonal antibody; (▲) anti-CD3 monoclonal antibody L2K; and (▼) control antibody MCO101.

3. Co-Binding Experiment of Bispecific Antibody-Mediated Immune Cells and Tumor Cells Cultured HCT116 and Jurkat cells were collected by centrifugation, washed twice with PBS and stained with CFSE and PKH-26 respectively. In the meantime, the bispecific antibody was diluted according to the concentration beginning from 10 ug/ml and ten-fold gradient dilution to obtain twelve concentration gradients for later use. The stained HCT116 and Jurkat cells were centrifuged to remove supernatant, washed twice with PBS+1% FBS, and then resuspended to $4 \times 10^6$ cell/ml with PBS+1% FBS respectively, cells were uniformly mixed according to a ratio of 1:1 and plated in a 96-well plate each well of which was loaded with 50 ul ($2 \times 10^5$ cells), 50 ul of diluted bispecific antibody was added, and cells were incubated for 1 hour at room temperature; and supernatant was removed by centrifugation, the cells were washed twice with PBS and resuspended with 100 ul PBS finally, and the ratio of double positive cells was analyzed through detection on an instrument and was calculated by using software GraphPadPrism 5.0. The result displayed that in case of no M701, the ratio of bifluorescence via flow cytometer detection was very low (as shown in FIG. 7); under the condition of adding the EpCAM×CD3 bispecific antibody M701, the ratio of bifluorescence via flow cytometer detection reached 27.5%, which indicated that M701 could simultaneously bind to EpCAM-positive HCT cells and CD3-positive Jurkat cells and promote the co-aggregation of the two kinds of cells to form an immune killer complex.

EXAMPLE 4

Determination of Thermal Stability of Bispecific Antibody

1. Tm Value Determination of Bispecific Antibody

Figure 8:
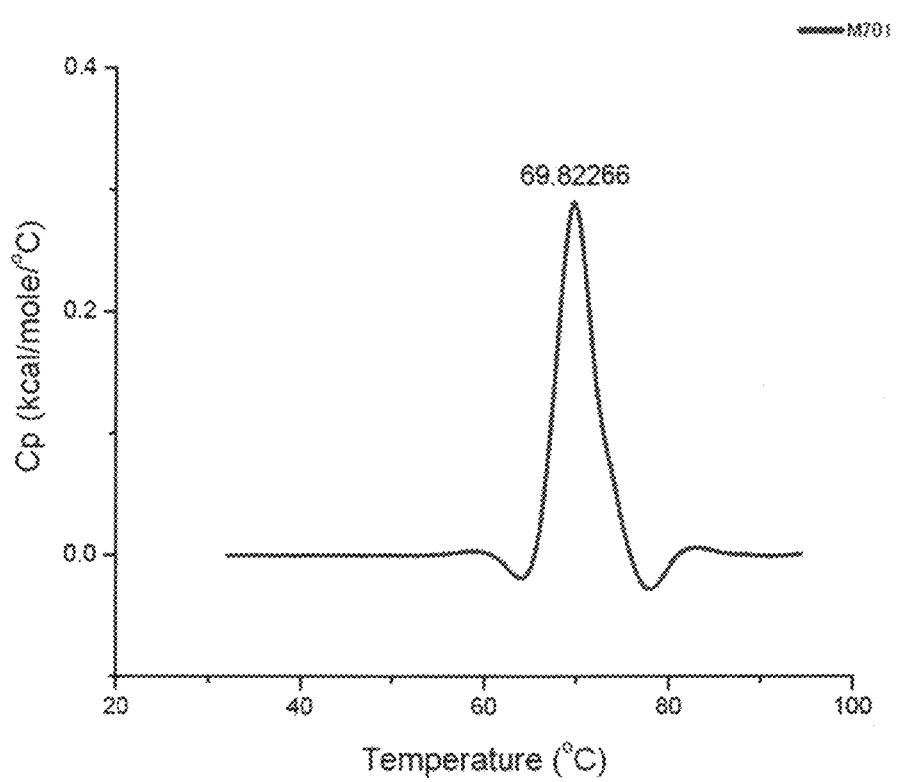
FIG. 8 is a Tm value result diagram of scanning survey for the EpCAM×CD3 MSBODY bispecific antibody by using a differential scanning calorimeter.

The thermal stability of the bispecific antibody was determined by a differential scanning calorimeter (MicroCal VP-DSC, GE Company), a bispecific antibody sample was displaced in a PBS buffer solution after being purified, and calorimetric scanning data was obtained by scanning at a heating velocity of 60° C./hour from 10° C. to 100° C. with the PBS buffer solution as a control. According to the scanning result displayed in FIG. 8, the Tm value of the bispecific antibody was about 70° C., which showed favorable thermal stability.

2. Thermal Challenge Experiment of Bispecific Antibody

Figure 9:
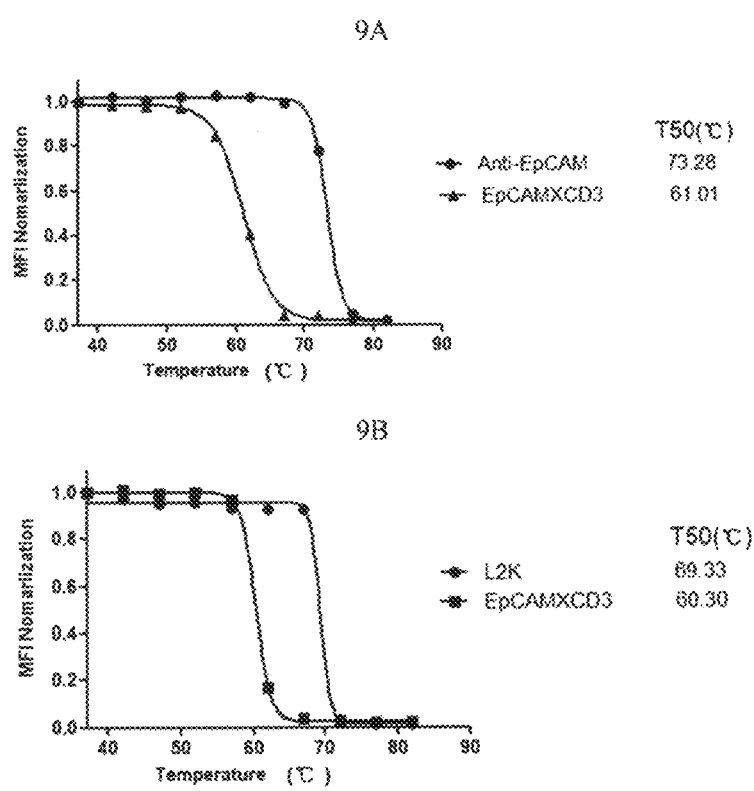
FIG. 9 refers to an activity detection result of the antibody after heat treatment, 9A. binding activity detection with EpCAM; (●) anti-EpCAM monoclonal antibody; (▲) EpCAM×CD3 MSBODY bispecific antibody; 9B. binding activity detection with CD3; (●) anti-CD3 monoclonal antibody L2K; and (■) EpCAM×CD3 MSBODY bispecific antibody.

The single chain antibody fragment (ScFv) was formed by connecting a heavy chain variable region and a light chain variable region through a connecting peptide ($Gly_4Ser_3$). However, it was reported that the inherent instability of ScFv could possibly affect the quality of an antibody drug (Michaelson JS1, etc., Anti-tumor activity of stability-engineered IgG-like bispecific antibodies targeting TRAIL-R2 and LTbetaR. MAbs. 2009 March-April; 1(2):128-41.). Therefore, the antibody was diluted to 0.4 mg/ml and was respectively treated for 1 h by a PCR instrument at 4° C., 37° C., 42° C., 47° C., 52° C., 57° C., 62° C., 67° C., 72° C., 77° C. and 82° C. with 15 ul each tube. The supernatant was taken by centrifugation, and the flow cytometer detection was performed according to the following steps: collecting a single cell suspension, adding into a 96-well plate with $3 \times 10^5$ cell/well, adding various processing antibodies, then adding a fluorescent secondary antibody, and carrying out flow cytometer detection on an instrument, wherein the detection result was as shown in FIG. 9, the thermal stability of the Anti-EpCAM and the EpCAM×CD3 MSBODY bispecific antibody, both of which bound to EpCAM, respectively, was determined as shown in FIG. 9A, and the $T_{50}$ values of both were 73.28 and 61.01 respectively; and the thermal stability of the L2K and the EpCAM×CD3 MSBODY bispecific antibody, both of which bound to the CD3 antibody respectively, was determined as shown in FIG. 9B, wherein the $T_{50}$ values were 69.33 and 60.30 respectively, both of which displayed better thermal stability.

EXAMPLE 5

Bispecific Antibody-Mediated In Vitro Cell-Killing Detection

1. PBMC Cell Separation and CIK Cell Culture

Fresh anti-freezing human blood was subject to 400 g centrifugal for 5 min and supernatant was discarded. 10-fold cell volume of red blood cell lysis buffer was added to the human blood, uniformly mixed by slightly blowing and beating, and subject to lysis at room temperature or on ice for 4-5 minutes during which appropriate shaking was needed so as to promote red blood cell lysis. 400 g centrifugal was performed for 5 min at 4 □, and red supernatant was discarded. If the red cell lysis was not complete, the step 2 and step 3 were repeated once. Washing was performed for 1-2 times. 5-fold cell sedimentation volume of PBS was added, cells were resuspended to obtain sediment and subject to 400 g centrifugal for 2-3 minutes at 4□, and then supernatant was discarded. The steps were repeated once if necessary and washing was performed for 1-2 times in total. The cells were resuspended to obtain sediment with appropriate 4□ precooled PBS according to experiment demands, and then subsequent experiments, such as counting can be performed.

Figure 10:
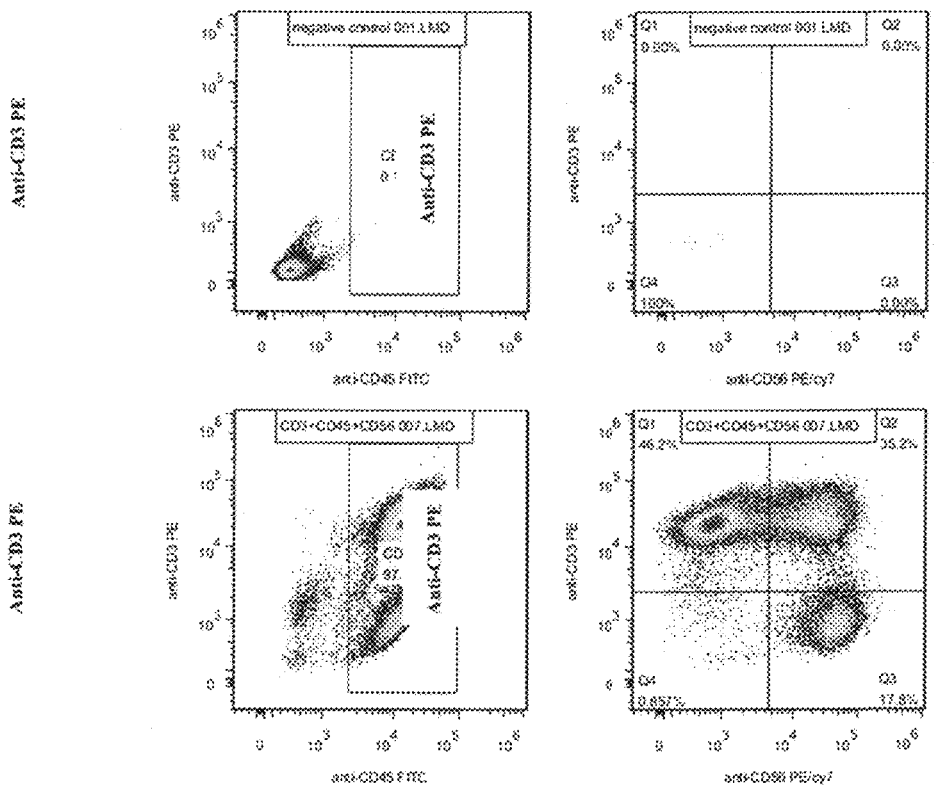
FIG. 10 is a CIK phenotype detection result diagram at the right corner of which double positive NK cells of CD3 and CD56 are located.

CIK cells were cultured according to the following steps: replenishing each portion of cells to 30 ml by using a CIK cell initiation culture solution (a serum-free X-Vivo cell culture solution+750 IU/ml IFN-γ±2% autologous plasma), adding the cells to a 75 $cm^2$ culture flask, and culturing the cells at 37° C. in a 5.0% $CO_2$ humidified incubator; after culture for 24 hours, adding 1 ml of CIK cell stimulation factor mixed solution (a serum-free X-Vivo cell culture solution+75 ng/ml anti-human CD3ε, 750 IU/ml IL-2 and 0.6 ng/ml IL-1α), and continuously culturing at 37° C. in the 5.0% $CO_2$ humidified incubator; as concerned in the following steps, determining the matters, such as replenishing of solutions (serum-free X-Vivo cell culture solution+750 IU/ml IL-2±2% autologous plasma) and bottling according to the growth situation of CIK cells to basically maintain the cells to grow at a density about $2*10^6$/ml; and finally, carrying out phenotypic detection, including CD3, CD56, CD4 and CD8, on the collected CIK cells, by using a flow cytometry FC500 and detecting the expression situations of these cell surface antigens in the CIK cells. The detection result was as shown in FIG. 10, the phenotype result displayed that the CIK cell had over 35% CD3 and CD56 double positive, and the cultured cell had favorable NK T cell ratio.

Figure 11:
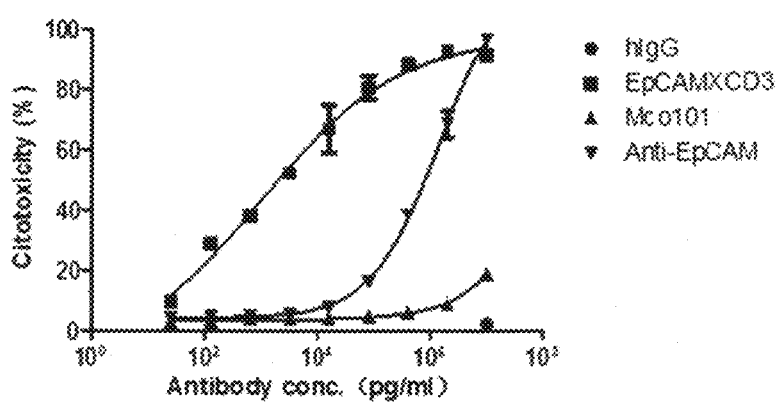
FIG. 11 is a killing effect result diagram of effector cells CIK on target cells HCT116 in the presence of different concentrations of antibodies in the flow cytometry detection; (■) EpCAM×CD3 MSBODY bispecific antibody; (▲) Mco101:control 4420×CD3 bispecific antibody; (▼) Anti-EpCAM: anti-EpCAM monoclonal antibody; and (●) hIgG: human IgG. EpCAM×CD3.
Figure 12:
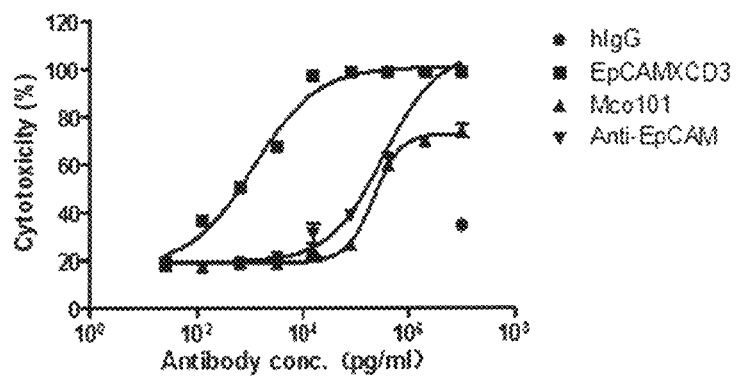
FIG. 12 a killing effect result diagram of effector cells CIK on target cells NCI-N87 in the presence of different concentrations of antibodies in the flow cytometry detection; (■) EpCAM×CD3 MSBODY bispecific antibody; (▲) Mco101:control 4420×CD3 bispecific antibody; (▼) Anti-EpCAM: anti-EpCAM monoclonal antibody; and (●) hIgG: human IgG.

2. Tumor Cell-Killing Detection of Bispecific Antibody-Effectively Mediated EpCAM Cells A single-cell suspension was prepared by digesting HCT116 or NCI-N87 cells with trypsin. The HCT116 or NCI-N87 cells were stained with CFSE with the final concentration being 5 uM, and the cells were resuspended to $2 \times 10^5$/ml with 10% FBS-1640 cultured by these cells after staining, and cultured over night in a 90-well plate according to $2 \times 10^4$ cell/well, namely 100 ul/well. According to the experiment design, the cultured CIK cells were added according to 50 ul/well, control wells were set, and the same volume of culture medium was fed into wells in which no CIK cells need to be added. The corresponding antibody was added with 50 ul/well according to the experiment design while the CIK cells were added, and the same volume of culture medium was fed into wells in which no antibody needs to be added. After 48 hours, the 96-well plate was taken out, cells of each well were digested with trypsin to form the single cell suspension, and correspondingly, all the supernatants and the cell suspension in this process were collected into 1.5 ml EP tubes and subject to 500×g centrifugal for 5 minutes. The supernatant was discarded, and 150 ul 1% FBS-PBS was added to each well, and then cells were resuspended and uniformly mixed. PI (the final concentration of 1 ug/ml) was added 10-15 min before each tube was put on an instrument for fluorescence-activated cell sorting, and the proportion of CFSE and PI double positive cells, namely the death rate of target cells HCT116 or NCI-N87 was detected on the instrument for fluorescence-activated cell sorting (the result was as shown in FIG. 11 and FIG. 12). The cell killing result displayed that the EpCAM× CD3 MSBODY bispecific antibody-mediated CIK cells displayed a favorable killing effect on tumor cells, and both the maximum killing efficiency and EC50 were remarkably higher than those of the Anti-EpCAM monoclonal antibody.

Figure 13:
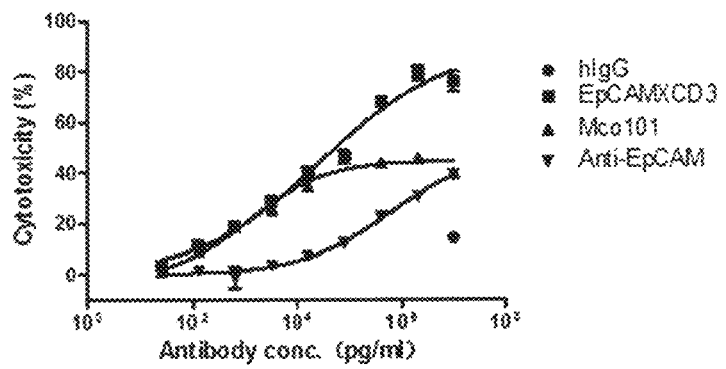
FIG. 13 is a killing effect result diagram of effector cells PBMC on target cells HCT116 in the presence of different concentrations of antibodies in the flow cytometry detection; (■) EpCAM×CD3 MSBODY bispecific antibody; (▲) Mco101:control 4420×CD3 bispecific antibody; (▼) EpCAM: EpCAM monoclonal antibody; and (●) hIgG: human IgG.
Figure 14:
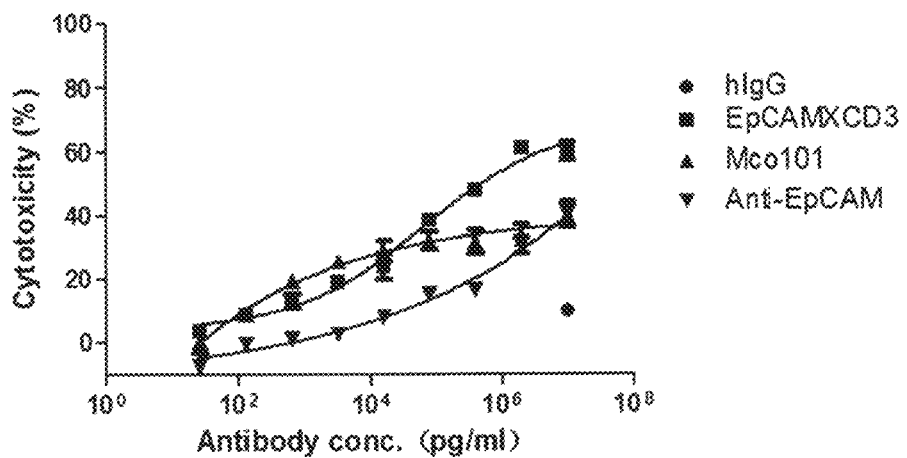
FIG. 14 is a killing effect result diagram of effector cells PBMC on target cells NCI-N87 in the presence of different concentrations of antibodies in the flow cytometry detection; (■) EpCAM×CD3 MSBODY bispecific antibody; (▲) Mco101:control 4420×CD3 bispecific antibody; (▼) EpCAM: EpCAM monoclonal antibody; and (●) hIgG: human IgG.

3. Tumor Cell-Killing Detection of Bispecific Antibody-Effectively Mediated PBMC Cells A single-cell suspension was prepared by digesting HCT116 or NCI-N87 cells with trypsin. The HCT116 or NCI-N87 cells were stained with CFSE with the final concentration being 5 uM (the staining step refers to protocol-1 CFSE staining), and the cells were resuspended to $2 \times 10^5$/ml with 10% FBS-1640 cultured by these cells after staining, and cultured over night in a 90-well plate according to $2 \times 10^4$ cell/well, namely 100 ul/well. According to the experiment design, the cultured CIK cells were added according to 50 ul/well, control wells were set, and the same volume of culture medium was fed into wells in which no CIK cells need to be added. The corresponding antibody was added with 50 ul/well according to the experiment design while the CIK cells were added, and the same volume of culture medium was fed into wells in which no antibody needs to be added. After 48 hours, the 96-well plate was taken out, cells of each well were digested with trypsin to form the single cell suspension, and correspondingly, all the supernatants and the cell suspension in this process were collected into 1.5 ml EP tubes and subject to 500×g centrifugal for 5 minutes. The supernatant was discarded, and 150 ul 1% FBS-PBS was added to each well, and then cells were resuspended and uniformly mixed. PI (the final concentration of 1 ug/ml) was added 10-15 min before each tube was put on an instrument for fluorescence-activated cell sorting, and the proportion of CFSE and PI double positive cells, namely the death rate of target cells HCT116 or NCI-N87 was detected on the instrument for fluorescence-activated cell sorting (the result was as shown in FIG. 13 and FIG. 14). The cell killing result displayed that the EpCAM× CD3 MSBODY bispecific antibody-mediated CIK cells displayed a favorable killing effect on tumor cells, and both the maximum killing efficiency and EC50 were remarkably higher than those of the Anti-EpCAM monoclonal antibody.

EXAMPLE 6

Pharmacological Detection of Bispecific Antibody for Killing Subcutaneous Xenograft Tumors A tumor xenograft model was established by mixing $5 \times 10^6$ SW480 and $5 \times 10^6$ CIK cells and growing at right flanks of female NOD/SCID mice through subcutaneous inoculation (N=8 groups). These mice were randomly grouped within two hours, and then, the mice in an antibody therapy group were administrated with EpCAM×CD3 MSBODY through tail intravenous injection according to the dosages of 2 mg/kg, 1 mg/kg and 0.5 mg/kg. The control groups were as follows: the mice in one group were administrated with 2 mg/kg anti-EpCAM monoclonal antibody and the mice in other group were administrated with MSBODY (4420×CD3) as independent control. The control MSBODY was a constructed by an anti-fluorescein antibody (4-4-20)(Kranz D M, Voss E W Jr., Partial elucidation of an anti-hapten repertoire in BALB/c mice: comparative characterization of several monoclonal antifluoresceyl antibodies. Mol Immunol. 1981; 18(10): 889-898). Administration was performed in the second day and the fourth day with unchanged dosage. The animals in the corresponding control group were administrated with PBS through intravenous injection. The volumes of the tumors were measured every three days and calculated from digital caliper measurements as ½×length×width×width (in $mm^5$).

Figure 15:
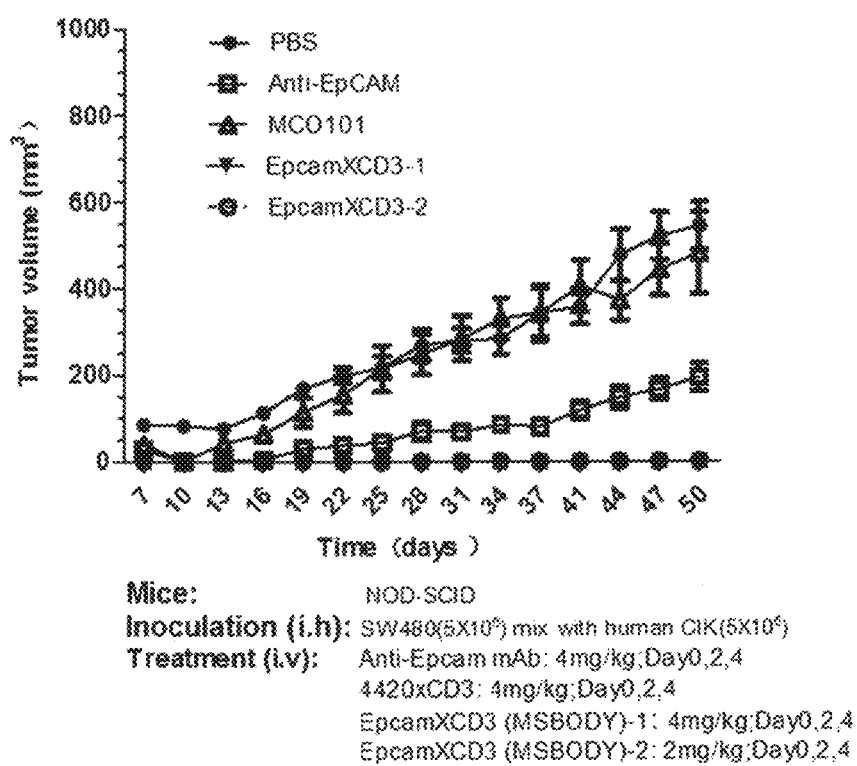
FIG. 15 refers to a pharmacological experiment result in the bispecific antibody, mice: NOD-SCID; inoculation (i. h): associative inoculation of SW480($5\times10^6$) and human CIK ($5\times10^6$): administration (i. v): EpCAM mAb: 4 mg/kg; Day (0,2,4), 4420×CD3: 4 mg/kg; Day (0,2,4),EpCAM×CD3 (MSBODY)-1: 4 mg/kg; Day (0,2,4),EpCAM×CD3(MSBODY)-2: 2 mg/kg; Day (0,2,4); (■) represents PBS which is administrated just through caudal vein; (□) anti-EpCAM monoclonal antibody; (Δ) 4420×CD3 unrelated control bispecific antibody; (▼) M701-1:EpCAM×CD3 SMBODY bispecific antibody 4 mg/kg concentration group; and (○) M701-2: EpCAM×CD3 SMBODY bispecific antibody 2 mg/kg concentration group.

The antitumor effect estimation of EpCAM×CD3 MSBODY in the body was finished through an adoptive transfer xenograft tumor model. SW480 cells of a gastric cancer cell line were used for establishing a xenograft tumor model on immunodeficient mice NOD/SCID, and the human CIK cells were obtained by simulative culture after the peripheral blood mononuclear cells were separated, and the two kinds of cells were associatively inoculated according to a proportion of 1:1. As shown in FIG. 15, the PBS group, the control anti-EpCAM antibody and the 4420×CD3 antibody for therapy have no remarkable inhibition on the tumor growth, but in the same experiment, no tumor growth was found in an EpCAM×CD3 (2 mg/kg, 4 mg/kg) treatment group, and therefore the tumor growth can be remarkably inhibited via EpCAM×CD3 MSBODY-mediated immune tumor killing. As expected, even CD3 specific molecules were reserved, the MSBODY molecules MC0101 (4420×CD3) lacking EpCAM specificity cannot displayed a remarkable antitumor activity in an in vivo experiment.

It should be understood that the present invention disclosed here is not only limited to describe specific methods, solutions and matters because all of these can change. It also should be realized that terms concerned herein are only for the purpose of describing specific embodiments, but do not have an intend of limiting the scope of the present invention, and the scope of the present invention is only limited by claims attached.

Those skilled in the art should realize or confirm that many equivalents concerned in specific embodiments of the present invention in this text are used within the conventional experiment range. These equivalents are intended to come within the scope of the appended claims.

What is claimed is:

1. A bispecific antibody, comprising:
   (a) a monovalent unit comprising a light chain-heavy chain pair which specifically binds to EpCAM, wherein the heavy chain comprises the amino acid sequence of SEQ ID NO: 1 and the light chain comprises the amino acid sequence of SEQ ID NO: 3: and
   (b) a single-chain unit which is a fusion peptide comprising a single-chain variable fragment (scFv) and an FC fragment which comprises a hinge region, a CH2 structural domain and a CH3 structural domain, wherein the single-chain unit has binding specificity to a surface antigen CD3, and wherein the single-chain unit comprises the amino acid sequence of SEQ ID NO: 5.

2. The bispecific antibody of claim 1, wherein the CH2 structural domain of the single-chain unit is positioned between the scFv fragment and the CH3 structural domain and the single-chain unit does not contain a CH1 structural domain.

* * * * *